Figure 1:
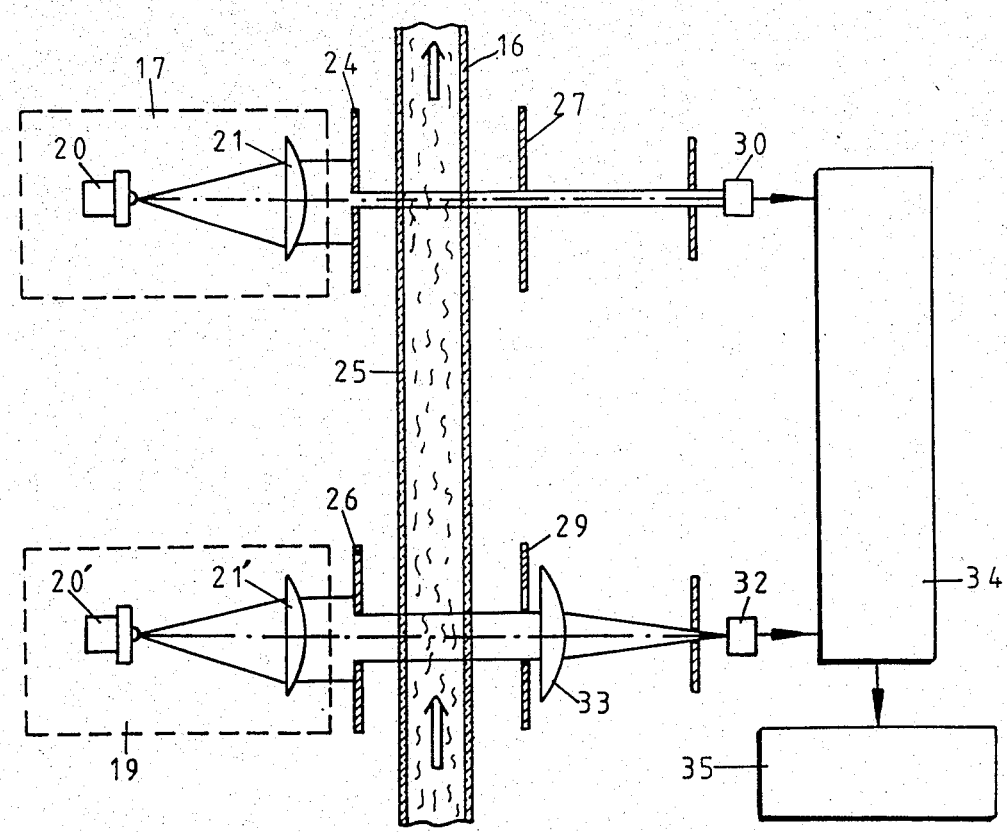

United States Patent [19]

Pettersson et al.

[11] Patent Number: 4,529,309
[45] Date of Patent: Jul. 16, 1985

[54] METHOD FOR DETERMINING THE AVERAGE RADIUS AND/OR THE AVERAGE LENGTH OF PARTICLES CARRIED BY A FLOWING MEDIUM

[75] Inventors: Jan G. T. Pettersson, Täby; Hakan I. Karlsson, Åkersberga, both of Sweden

[73] Assignee: Svenska Träforskningsinstitutet, Stockholm, Sweden

[21] Appl. No.: 425,446

[22] Filed: Sep. 28, 1982

[30] Foreign Application Priority Data

Oct. 1, 1981 [SE] Sweden .............................. 8105802

[51] Int. Cl.³ .............................................. G01N 15/02
[52] U.S. Cl. ........................................ 356/335; 356/342
[58] Field of Search ................. 356/335, 342; 250/573

[56] References Cited

U.S. PATENT DOCUMENTS

| | | | |
|---|---|---|---|
| 3,275,834 | 9/1966 | Stevens | 356/335 |
| 3,790,260 | 2/1974 | Stiller | 356/335 X |
| 3,818,200 | 6/1974 | Pilhofer | 356/335 X |
| 3,879,129 | 4/1975 | Inoue | 356/335 |
| 4,318,180 | 3/1982 | Lundqvist et al. | 356/442 X |

Primary Examiner—F. L. Evans
Assistant Examiner—Matthew W. Koren
Attorney, Agent, or Firm—Hill, Van Santen, Steadman & Simpson

[57] ABSTRACT

Fiber content measuring instruments having radiation detectors are used to indicate the average radius and/or the average length of particles in a flowing medium. In order to determine the average radius, a signal based on the alternating current voltage portion of the signal from a radiation detector having a high resolution is divided by a signal based on the direct current voltage portion and the signal from a radiation detector having the same or another resolution. In order to determine the average length a signal based on the alternating current voltage portion of the signal from the radiation detector having a low resolution is divided by a signal based on the alternating current voltage portion of the signal from the radiation detector having a high resolution.

12 Claims, 2 Drawing Figures

METHOD FOR DETERMINING THE AVERAGE RADIUS AND/OR THE AVERAGE LENGTH OF PARTICLES CARRIED BY A FLOWING MEDIUM

BACKGROUND OF THE INVENTION

1. Field of the Invention:

The present invention relates to an optical method for determining the average radius and/or the average length of particles, such as fibers, carried by a flowing medium.

2. Prior Art:

There are instruments which are used as particle content meters. In U.S. Pat. No. 4,110,044 such an instrument is described which includes a measuring head, by which particle content in a flowing medium is indicated. In U.S. Pat. No. 4,318,180 an instrument is disclosed having three measuring heads having mutually different resolutions which are used to measure the particle size distribution of particles in a flowing medium. These instruments are used to make measurements on fiber suspensions, and in particular on such suspensions which are used as basic material for paper manufacture.

Normally, the fibers in such a fiber suspension have a fairly predetermined relation between their thickness and their length. The results from the measurements in accordance with the teachings of U.S. Pat. No. 4,318,180 on the fiber suspensions are based on this relationship.

However, in order to provide different paper qualities the fibers in the fiber suspensions are sometimes preprocessed in some way. For instance they may pass through grinding operations. By these grinding operations the fibers are squeezed and twisted into bands and after this treatment the fiber radius and the fiber length have no longer a predetermined relationship to each other. It has become apparent that information especially about the average radius, but also about the average length of the fibers after grinding, gives a principal indication of the effectiveness of the grinding device.

SUMMARY OF THE INVENTION

In a deep study of the properties of the fibers, which are really indicated by the different output signals of the fiber content meters described in the U.S. patents mentioned above we have found that the logarithmic direct current voltage signal DC provided in the meter has an inverse relation to the radius of the particles in a suspension, while the logarithmic alternating current voltage signal AC has a relation to the particle length up to a predetermined length determined by the resolution of the fiber content meter. Thereafter it is independent of the length. The value of both signals is linearly dependent on the concentration of suspended particles.

In accordance with the invention, the indication of the average fiber radius is made by dividing the AC signal from a radiation detector having a small cross section for the radiation detected by the DC signal provided by said same radiation detector or by a second radiation detector having the same or some other cross section for the radiation detected. The indication of the average fiber length is made by dividing the AC signal from a radiation detector having a large cross section for radiation detected by the AC signal from a radiation detector having a small cross section for the radiation detected.

Thus in accordance with the invention for determining the average radius of the suspended fibers, a fiber content meter is used having such a high resolution that the signal AC based on the alternating current voltage from the measuring device is not influenced by variations in the length of the particles, and thus a division between the signal AC and the signal DC from the fiber content meter gives an indication of the average radius of the particles disposed in the suspension, on which a measurement has been made.

In order to have an indication of the average length of the particles still another fiber content meter is used. However, this meter has such a low resolution that the length of the fibers in the suspension is contained within the angle of sight of the optical detector. The resolution of an instrument is dependent on the cross section of the detected light going through the medium in such a way that a high resolution means a small cross section and a resolution means a wide cross section. In order to obtain the average length of the fibers, the signal AC from the fiber content meter head having a low resolution is divided by the signal AC from the fiber content meter having a high resolution.

ON THE DRAWINGS

Figure 2:
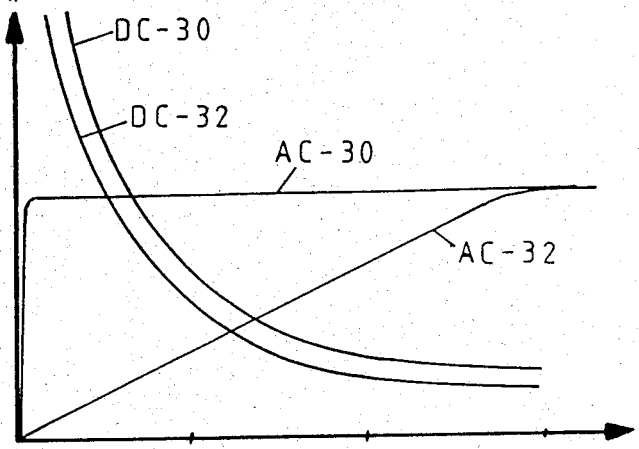

The invention is described in more detail below with reference to the accompanying drawing, in which FIG. 1 shows an embodiment of a device by which the method according to the invention is performed, and FIG. 2 shows diagrams of the signals AC used in accordance with the invention.

AS SHOWN IN THE DRAWINGS

In FIG. 1 an embodiment of a device is shown, by which the method in accordance with the invention is performed.

This drawing is a part of a view shown in U.S. Pat. No. 4,318,180. Two fiber content meter sets or heads 17, 19 are shown, of which the upper one 17 has a high resolution and the lower one 19 has a low resolution. Both meter heads operate in the following way. The radiation from a radiation source 20, 20' is emitted in a direction which intersects the direction of medium flow, and has a predetermined intensity which is substantially constant at least during a measuring operation. The radiation is subjected to certain optics to limit the cross-section thereof that can be detected, and to that end is collimated by a lens system 21, 21' diagrammatically shown as a lens. A diaphragm or aperture 24, 26 passes a beam of the collimated light through a cuvette 16 including a flowing fiber suspension having the fibers on which measurement is to be made. The description here is made on the basis of measurements on fibers in a fiber suspension, but our invention is applicable to measurement of other particles in a flowing medium, where the medium might be a liquid or gas. Preferably, the cuvette 16 has plane surfaces where the radiation passes. On the other side of the cuvette yet another diaphragm an aperture 27, 29 is disposed and, where required also a collector lens 33. The last mentioned unit 27 or 29 and 33 determines the angle of sight for a pair of radiation detectors 30, 32. The upper meter head in FIG. 1 has such a small angle of sight that the emitted radiation passes straight through the medium, and that the lengths of practically all fibers in the medium are longer than the base width inside the cuvette of a triangle having the angle of sight as a top angle. The lower meter set in FIG. 1 has such a wide angle of sight that the lengths of the fibers, that one can expect to have, lie well within said base width. The detected radiation is transformed into an electrical signal which varies in response to radiation intensity.

The outputs from the detectors 30, 32 are connected to a calculating circuit 34 which forms two signals DC and AC. Based on the signal from each one of the detectors this circuit makes the calculation $$DC = \ln(V'_{DC}/V_{DC})$$

where $V'_{DC}$ and $V_{DC}$ are the direct current voltage portions of the signal from the detector during measuring of a medium with suspended particles and during measuring of a medium without suspended particles, respectively. The value $V'_{DC}$ thus has been derived at an earlier measurement on a clear medium and has been stored in a memory included in the calculating circuit 34.

From the signal from each one of the detectors 30, 32 the circuit 34 makes the following calculation.

$$AC = \ln\left(\frac{V^2_{RMS}}{c_2} + 1\right)$$

or $$AC = \ln\left(\frac{V^2_{RMS}}{c_3} \cdot \frac{V^2_{DC}}{V'^2_{DC}} + 1\right)$$

which is the logarithmic alternating current voltage signal AC mentioned above and where $V^2_{RMS}$ is the square of the true effective R.M.S. of the alternating current voltage portion of the signal from the detector during measuring of a medium with particle, and $c_2$ and $c_3$ are constants.

In FIG. 2 the sensitivity of the calculated logarithmic alternating current voltage signal AC is shown as a function of the average fiber length in the fiber fraction for both meter head geometries as well as the sensitivity of the calculated direct current voltage signal DC as a function of the average radius of fiber fraction. By a study of these signals the following relation has been found to be valid:

$$DC = konc \cdot k/r$$

where k is a constant, which is dependent on the fibre content meter head geometry, konc is the fiber concentration in the medium and r is the average radius of the fibers.

For the signal AC the following relations have been found to be valid. For the linear oblique part of the curve $$AC = k_1 \cdot konc \cdot s$$

where $k_1$ is a constant, konc is the fiber concentration in the medium and s is the average length of the fibers.

For the part of the diagram of the signal AC where the curve is altogether on practically the same level then $$AC_2 = k_2 \cdot konc$$

i.e. on this part of the curve the signal strength is only dependent on the concentration.

As is apparent from the curve of the signal AC from the detector 30, the knee of the curve, i.e. the changeover from being oblique into being on practically the same level, lies on such a low fiber length level that the fiber length has not any practical influence on this signal. Then, since this signal is dependent on only the fiber concentration, the average fiber radius can be derived by dividing this signal with the signal DC from one of the meter sets, i.e.

$$r = AC_2/DC$$

and the average length s can be derived by dividing the signal AC from the fiber content meter head 19 having a low resolution with the signal AC from the fiber content meter head 17 having a high resolution, i.e.

$$s = AC_1/AC_2$$

In order to have an indication of the average radius of particles in a flowing medium, thus only one fiber content meter head having a high resolution is needed. In order to have an indication of the average length of the particles, two fiber content meter heads are needed, one of them having a low resolution and the other one a high resolution.

It is to be noted that the fiber content meter heads shown in FIG. 1 are only shown as an example of such heads and that different modifications might be made on the embodiment shown especially concering the optics.

We claim:

1. A method for determining the average radius and/or the average length of fibers carried by a flowing medium by using at least one radiation source for emitting and directing radiation through the medium in a direction having an angle different from 0° to the direction of flow of the medium, the intensity of the radiation at least during a measuring operation being substantially constant and predetermined; first and second radiation detectors for receiving and indicating radiation emitted from respective radiation sources and passing straight through said medium, and for transforming the detected radiation into an electrical signal varying in dependence on the radiation intensity; optics disposed between said radiation source and said first detector for limiting the cross section of the radiation passing through the medium emitted by said radiation source and detected by said first detector, said second radiation detector receiving radiation of a larger cross-section then said first radiation detector, and a calculation unit connected to said detectors, which forms two signals DC and AC in accordance with the formulas $$DC = \ln(V'_{DC}/V_{DC})$$

$$AC = \ln\left(\frac{V^2_{RMS}}{c_2} + 1\right)$$

where $V'_{DC}$ and $V_{DC}$ are respectively the direct current voltage portion of the signal from said first detector during measuring of a medium with particles and during measuring of a medium without particles, $V^2_{RMS}$ is the square of the true effective value (R.M.S.) of the alternating current voltage portion of the signal from said first detector during measuring of a medium with particles, and $c_2$ is a constant, the determination of the average fiber radius being made by dividing the signal AC from said first radiation detector for radiation having a small cross section by the signal DC provided by said same detector and the determination of the average fiber length being made by dividing the signal AC from said second detector for radiation having a large cross section by the signal AC from said first detector for radiation having a small cross section.

2. A method for determining the average radius and/or the average length of particles carried by a flowing medium using at least one radiation source for emitting and directing radiation through the medium in a direction intersecting the direction of flow of the medium, the intensity of the radiation at least during a measuring operation being substantially constant and predetermined; first and second radiation detectors for receiving radiation passing straight through said medium, and for transforming the detected radiation into electrical signals varying in dependence on the radiation intensity; optics disposed between said radiation source and said first detector for limiting the cross-section of the radiation passing through the medium; said second radiation detector receiving radiation of a larger cross-section than said first radiation detector; and a calculation unit connected to said detectors, which forms two signals DC and AC; said average particle radius being determined by dividing the AC signal from said first detector of radiation having a small cross-section by the DC signal provided by said same detector; and the average particle length being determined by dividing the AC signal from said second detector for radiation having a large cross-section by the AC signal from said first detector for said radiation having a small cross-section.

3. A method for determining the average radius and/or the average length of fibers carried by a flowing medium by using at least one radiation source for emitting and directing radiation through the medium in a direction having an angle different from 0° to the direction of flow of the medium, the intensity of the radiation at least during a measuring operation being substantially constant and predetermined; first and second radiation detectors for receiving and indicating radiation emitted from said radiation source and passing straight through said medium, and for transforming the detected radiation into electrical signals varying in dependence on the radiation intensity; optics disposed between said radiation source and said first detector for limiting the cross-section of the radiation passing through the medium emitted by said radiation source and detected by said first detector; said second radiation detector receiving radiation of a larger cross-section than said first radiation detector; and a calculation unit connected to said detectors, which forms two signals DC and AC in accordance with the formulas $$DC = \ln (V'_{DC}/V_{DC})$$

$$AC = \ln \left( \frac{V^2_{RMS}}{c_3} \cdot \frac{V^2_{DC}}{V'^2_{DC}} + 1 \right)$$

where $V'_{DC}$ and $V_{DC}$ are respectively the direct current voltage portion of the signal from said first detector during measuring of a medium with particles and during measuring of a medium without particles, $V^2_{RMS}$ is the square of the true effective value (R.M.S.) of the alternating current voltage portion of the signal from said first detector during measuring of a medium with particles, and $c_3$ is a constant, the determination of the average fiber radius being made by dividing the AC signal from said first radiation detector for radiation having a small cross-section by the DC signal providing by said same detector; and the determination of the average fiber length being made by dividing the AC signal from said second detector for radiation having a large cross-section by the AC signal from said first detector for radiation having a small cross-section.

4. A method for determining the average radius and/or the average length of fibers carried by a flowing medium by using at least one radiation source for emitting and directing radiation through the medium in a direction having an angle different from 0° to the direction of flow of the medium, the intensity of the radiation at least during a measuring operation being substantially constant and predetermined; at least first and second radiation detectors for receiving and indicating radiation emitted from said radiation source and passing straight through said medium, and for transforming the detected radiation into electrical signals varying in dependence on the radiation intensity; optics disposed between said radiation source and said first detector for limiting the cross-section of the radiation passing through the medium emitted by said radiation source and detected by said first detector; said second radiation detector receiving radiation of a larger cross-section than said first radiation detector; and a calculation unit connected to said detectors, which forms two signals DC and AC in accordance with the formulas $$DC = \ln (V'_{DC}/V_{DC})$$

$$AC = \ln \left( \frac{V^2_{RMS}}{c_2} + 1 \right)$$

where $V'_{DC}$ and $V_{DC}$ are respectively the direct current voltage portion of the signal from said first detector during measuring of a medium with particles and during measuring of a medium without particles, $V^2_{RMS}$ is the square of the true effective value (R.M.S.) of the alternating current voltage portion of the signal from said first detector during measuring of a medium with particles, and $c_2$ is a constant, the determination of the average fiber radius being made by dividing the AC signal from said first radiation detector for radiation having the limited cross-section by the DC signal provided by a radiation detector other than said first detector; and the determination of the average fiber length being made by dividing the AC signal from one of said detectors for radiation having a large cross-section by the AC signal from the first detector for radiation having a small cross-section.

5. A method according to claim 4, said DC signal radiation detector having the same cross-section as said first detector.

6. A method according to claim 4, said DC signal radiation detector having a differing cross-section from that of said first detector.

7. A method for determining the average radius and/or the average length of fibers carried by a flowing medium by using at least one radiation source for emitting and directing radiation through the medium in a direction having an angle different from 0° to the direction of flow of the medium, the intensity of the radiation at least during a measuring operation being substantially constant and predetermined; first and at least one second radiation detectors for receiving and indicating radiation emitted from said radiation source and passing straight through said medium, and for transforming the detected radiations into electrical signals varying in dependence on the radiation intensity; optics disposed between said radiatin source and said first detector for limiting the cross-section of the radiation passing through the medium emitted by said radiation source and detected by said first detector; said second radiation detector receiving radiation of a larger cross-section than said first radiation detector; and a calculation unit connected to said detectors, which forms two signals DC and AC in accordance with the formulas $$DC = \ln(V'_{DC}/V_{DC})$$

$$AC = \ln\left(\frac{V^2_{RMS}}{c_3} \cdot \frac{V'^2_{DC}}{V^2_{DC}} + 1\right)$$

where $V'_{DC}$ and $V_{DC}$ are respectively the direct current voltage portion of the signal from said first detector during measuring of a medium with particles and during measuring of a medium without particles, $V^2_{RMS}$ is the square of the true effective value (R.M.S.) of the alternating current voltage portion of the signal from said first detector during measuring of a medium with particles, and $c_3$ is a constant, the determination of the average fiber radius being made by dividing the DC signal from said first radiation detector for radiation having a limited or small cross-section by the DC signal provided by one of said radiation detectors other than said first detector; and the determination of the average iber length being made by dividing the AC signal from one of said detectors for radiation having a large cross-section by the AC signal from the first detector for radiation having a small cross-section.

8. A method according to claim 7, said one DC signal radiation detector having the same cross-section as said first detector.

9. A method according to claim 7, said one DC signal radiation detector having a differing cross-section from that of said first detector.

10. A method for determining the average radius and/or the average length of particles carried by a flowing medium using at least one radiation source for emitting and directing radiation through the medium in a direction intersecting the direction of flow of the medium, the intensity of the radiation at least during a measuring operation being substantially constant and predetermined; first and at least one second radiation detectors for receiving radiation passing straight through said medium, and for transforming the detected radiation into an electrical signal varying in dependence on the radiation intensity; optics disposed between said radiation source and said first detector for limiting the cross-section of the radiation passing through the medium; said second radiation detector receiving radiation of a larger cross-section than said first radiation detector; and a calculation unit connected to said detectors, which forms an AC and DC signal; said average particle radius being determined by dividing the AC signal from said first detector of radiation having a small cross-section by the DC signal provided by one of said radiation detectors other than said first detector; and the average particle length being determined by dividing the DC signal from one of said detectors for radiation having a large cross-section by the AC signal from said first detector for radiation having a small cross-section.

11. A method according to claim 10, said one DC signal radiation detector having the same cross-section as said first detector.

12. A method according to claim 10, said one DC signal radiation detector having a differing cross-section from that of said first detector.

* * * * *